United States Patent [19]

Seely et al.

[11] Patent Number: 4,978,764

[45] Date of Patent: Dec. 18, 1990

[54] METHOD FOR AMMOXIDATION OF PARAFFINS

[75] Inventors: Michael J. Seely, Twinsburg; Maria S. Friedrich, Lyndhurst; Dev D. Suresh, Hudson, all of Ohio

[73] Assignee: The Standard Oil Company, Cleveland, Ohio

[21] Appl. No.: 411,989

[22] Filed: Sep. 25, 1989

[51] Int. Cl.$^5$ ............................................ C07C 253/24
[52] U.S. Cl. ..................................................... 558/319
[58] Field of Search ......................................... 558/319

[56] References Cited

U.S. PATENT DOCUMENTS

| | | | |
|---|---|---|---|
| 3,118,928 | 1/1964 | Garrison, Jr. | 558/319 |
| 3,670,008 | 6/1972 | Taylor | 558/319 |
| 3,686,267 | 8/1972 | Taylor | 558/319 |
| 3,833,638 | 9/1974 | Knox et al. | 558/319 |
| 4,323,520 | 4/1982 | Hardman et al. | 558/319 |
| 4,767,739 | 8/1988 | Glaeser et al. | 558/319 X |
| 4,835,125 | 5/1989 | Glaeser et al. | 558/319 X |
| 4,843,055 | 6/1989 | Glaeser et al. | 58/319 X |

Primary Examiner—Joseph Paul Brust
Attorney, Agent, or Firm—C. S. Lynch; D. J. Untener; L. W. Evans

[57] ABSTRACT

Disclosed is a process f9or making an α, β-unsaturated mononitrile by the catalytic reaction of a paraffin containing 3-5 carbon atoms with molecular oxygen and ammonia by catalytic contact of the foregoing reactants in a reaction zone with a metal oxide catalyst composition that has 10-90 weight percent of a diluent/support and 90-10 weight percent of a catalyst containing the elements indicated by the empirical formula, $$A_a D_d Bi_c Fe_f Mo_{12} O_x$$

in the proportions indicated by the said formula, said diluent/support containing 10 to 100 weight percent $Al_2O_3$ and zero to 90 weight percent $SiO_2$ wherein A is one or more of Li, Na, K, Rb, Cs, Tl B, W, Sn and La;

D is one or more of Cr, Sb, Pb, P, Cu, Ni, Co, Mn and Mg;

a is zero to 10;

c is 0.1 to 10;

d is zero to 10; and f is 0.2 to 10; and wherein the reactants fed to the reaction zone contain a mole ratio of said paraffin:$NH_3$ in the range from 2 to 16 and a mole ratio of said paraffin to $O_2$ in the range from 1 to 10.

19 Claims, No Drawings

METHOD FOR AMMOXIDATION OF PARAFFINS

This invention relates to an improved process for the catalytic ammoxidation of paraffins containing from 3 to 5 carbon atoms to α,β-unsaturated mononitriles, especially paraffins containing 3 to 4 carbon atoms. Most important is the ammoxidation of isobutane to methacrylonitrile and, especially, of propane to acrylonitrile.

Because of the price differential between propylene and propane an economic incentive exists for the development of a viable catalytic process for conversion of propane to acrylonitrile.

Early attempts in the prior art to develop an efficient process for the ammoxidation of propane to acrylonitrile produced either insufficient yields or processes that necessitated adding halogen promoters to the feed. The latter procedure would require not only reactors made of special corrosion resistant materials, but also the quantitative recovery of the promoter. The added costs thus eliminated the advantage of the propane/propylene price differential.

It is thus an object of the present invention to provide an improved process for the ammoxidation of paraffins to unsaturated mononitriles and the corresponding mono-olefins.

Still another object is to provide an improved catalytic ammoxidation process for making unsaturated mononitriles from lower paraffins without the use of halogen promoters.

Other objects, as well as aspects, features and advantages, of the present invention will become apparent from a study of the accompanying disclosure and the claims.

These and other objects are achieved by the present invention according to one aspect of which there is provided a process for making an α, β-unsaturated mononitrile by the catalytic reaction of a paraffin containing 3-5 carbon atoms with molecular oxygen and ammonia by catalytic contact of the foregoing reactants in a reaction zone with a metal oxide catalyst composition that has 10-90 weight percent of a diluent/support and 90-10 weight percent of a catalyst containing the elements indicated by the empirical formula,

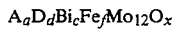

$$A_a D_d Bi_c Fe_f Mo_{12} O_x$$

in the proportions indicated by the said formula, said diluent/support containing 10 to 100 weight percent $Al_2O_3$ and zero to 90 weight percent $SiO_2$, usually at least 20 weight percent $Al_2O_3$ and at most 80 weight percent $SiO_2$, wherein
A is one or more of Li, Na, K, Rb, Cs, Tl, B, W, Sn and La;
D is one or more of Cr, Sb, Pb, P, Cu, Ni, Co, Mn and Mg;
a is zero to 10;
c is 0.1 to 10;
d is zero to 10; usually at least 1, and
f is 0.2 to 10; usually at least 0.6, and
wherein the reactants fed to the reaction zone contain a mole ratio of said paraffin:$NH_3$ in the range from 2 to 16 and a mole ratio of said paraffin to $O_2$ in the range from 1 to 10.

In particular, we have discovered that the present catalyst compositions containing alumina as a support or diluent with or without silica, is greatly activated to promote the ammoxidation of paraffins by the presence of the alumina as compared with the same catalyst compositions containing no diluent/support or containing only silica diluent/support. Thus, the latter compositions are nearly inactive to promote the ammoxidation reaction and the addition of alumina to the same compositions produces excellent ammoxidation catalysts for the paraffins.

We regard as particularly useful catalysts of the invention those catalysts wherein A includes one or more of Li, Na, K, Cs and W; we have also found particularly desirable those catalysts wherein D includes one or more of Cr, Sb, P, Ni, Co, Mn and Mg; all with respect to the empirical formula noted hereinbefore.

In the catalyst compositions of the invention the empirical formula denotes the atomic ratios of the listed elements and does not, of course, connote any particular chemical compound, nor indicate whether the elements are present as a mixture of individual oxides or as a complex oxide or oxides, or what separate crystalline phases or solid solutions may be present. However, the catalyst contains the elements and proportions indicated by the foregoing formula. Similarly, the designation of certain oxides, such as "silica" or "alumina" or $SiO_2$ or $Al_2O_3$, as supports or diluents is merely in accordance with convention in the inorganic oxide catalyst art, and such designations refer to compounds often regarded as supports in the catalyst art. Such designations, however, do not mean that the element involved is actually present as a simple oxide. Indeed, such elements may at times by present as a complex oxide with one more than one, or all of the elements in the foregoing empirical formula, which complex oxides form during the process for preparing the catalyst composition.

In the ammoxidation of the present invention, the reaction is carried out in the gas phase by contacting a mixture containing the paraffin, ammonia and molecular oxygen, and inert diluent, if any, conveniently in a fixed bed of the catalyst, or a gravity flowing bed, a fluidized bed or a fast transport reactor mode.

The mole ratio of $O_2$ to $NH_3$ fed to the reaction zone is usually in the range from 1–10 (more often 1–5), and the mole ratio of inert gaseous diluent to paraffin is usually in the range from zero–20 (more often zero–12); of course, even higher molar ratios say up to 50 mols diluent to 1 mols paraffin, can be used but are usually uneconomical.

In the present process, when applied to propane ammoxidation, a small amount of propylene is produced in relation to the unreacted propane in the effluent. Thus the propane effluent containing propylene in the amount of up to 8 mole percent, but usually no more than 6 mole percent, of the amount of propane plus propylene can comprise substrate feed to the present process.

And in general the $C_3$ to $C_5$ alkane feed to the reaction zone of the process of the present invention can contain one or more $C_3$ to $C_5$ olefins. The $C_3$ to $C_5$ olefin content of the feed to the present ammoxidation process can contain from zero to 8 mole percent of such olefin(s), based on the moles of $C_3$ to $C_5$ paraffin plus olefins fed, and this feed can be from any source. However, larger amounts of $C_3$ to $C_5$ olefins may be present in the substrate paraffin feed, but the usual proportions are as stated, and the usual olefin is that corresponding to the particular paraffin fed to the reaction zone of the present process.

Examples of inert diluents useful in the reaction zone are $N_2$, He, $CO_2$, $H_2O$ and Ar. The excess paraffin, such as propane, over the stoichiometric amount of $O_2$ and $NH_3$ acts, of course, as a further diluent.

The reaction temperature range can vary from 350° to 700°°, but is usually 440° to 550° C. The latter temperature range is especially useful in the case of propane ammoxidation to acrylonitrile.

The average contact time can often be from 0.01 to 10 seconds, but is usually from 0.02 to 10 seconds, more usually from 0.05 to 5 seconds.

The pressure of the reaction usually ranges from 1 to 45 psig. Most often, pressure is somewhat above atmospheric, i.e. 1 to 15 psi.

In any event, the pressure, temperature and contact times are not the essence of the invention and can be outside these ranges. The most advantageous combination of these conditions for a given desired result from a given feed can be determined by routine experimentation.

The nitrile products of the present process contain one C to C double bond and one nitrile group. The desired olefin products contain one double bond and the same number of C atoms as the paraffin feed.

The following examples of the invention are exemplary and should not be taken as in any way limiting.

In the following ammoxidation examples 1-7 summarized in Table 1, the catalyst is in a tubular ⅜ inch I.D. stainless steel fixed bed reactor. Pressure was slightly above atmospheric. The reactor is equipped with a preheat leg and is immersed in a temperature controlled molten salt bath. The feed is fed to the catalyst for at least one hour before collection of product; the runs of each example last 30-60 minutes during which the product is collected for analysis.

Also summarized in Table I are Examples 8 and 9. These runs were fluidized bed ammoxidations in a 1.5 inch laboratory reactor. The feeds to the two reactions were quite different, as will be seen from Table 1. Also, Run 8 was effected at just above atmospheric, while Run 9 was effected at 10 psig.

Although comparative Example 1 and Example 2 were effected at a contact time less than optimum, the drastic improvement using an alumina-containing catalyst in the latter run is illustrated in conversion of propane and in yields and selectivities for acrylonitrile, propylene and HCN products.

CATALYST EXAMPLE 1

(Comparative)

In this example "parts" means parts by weight.

The following reagents were used to make a catalyst of the empirical formula

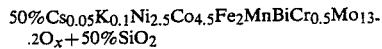

| Reagent | Parts |
|---|---|
| $CsNO_3$ - 10% Soln. | 1.46 |
| $KNO_3$ - 10% Soln. | 1.52 |
| $Ni(NO_3)_2.6H_2O$ | 10.90 |
| $Co(NO_3)_2.6H_2O$ | 19.65 |
| $Fe(NO_3)_3.9H_2O$ | 12.12 |
| $Mn(NO_3)_2$ - 50% Soln. | 5.37 |
| $Bi(NO_3)_3.5H_2O$ | 7.28 |
| $CrO_3$ | 0.75 |
| $(NH_4)_6Mo_7O_{24}.4H_2O$ | 34.96 |
| $SiO_2$ Sol, 40% | 109.55 |

The ferric nitrate and 10 parts of water are melted on a hot plate with stirring. The other nitrates are then added, one at a time, in the order listed: Mn—, Bi—, Co—, Ni—, K— and Cs—nitrate. The dark brown dispersion is stirred with heating at 60° C.

The ammonium-hepta-molybdate is dissolved in 200 parts of water at 60° C. The silica sol is then added followed by the $CrO_3$, which had been diluted with 10 parts of water. An orange dispersion is formed.

The nitrates dispersion is added slowly to the Mo—Si—Cr solution, forming a yellow slurry. This is evaporated on a hotplate with constant stirring until it starts to thicken. It is then dried at 120° C overnight, heat-treated at 290° C. for 3 hours and at 425° C. for 3 hours, ground to a 20-35 mesh size, and calcined at 610° C. for 3 hours.

CATALYST EXAMPLE 2

This was the same as Catalyst Example 1 except that only one-half the weight of silica sol was used, an equal amount of alumina sol replaced the removed $SiO_2$, and the alumina sol was added last, after addition of all the nitrates. The catalyst composition was

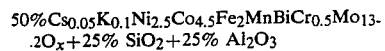

CATALYST EXAMPLE 3

This was the same as Catalyst Example 1 except that the composition was

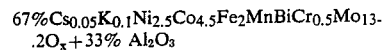

addition of $SiO_2$ was omitted, and the $Al_2O_3$ was added as a sol after addition of all of the nitrates.

CATALYST EXAMPLE 4

A catalyst having the composition

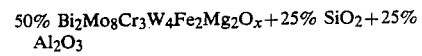

was prepared as follows:

5.86 g of $(NH_4)_6Mo_7O_{24}.4H_2O$ was dissolved in 200 cc of warm $H_2O$; 4.53 g of Ammonium-meta-tungstate (85% $WO_3$) was dissolved in $H_2O$, and added. 4.98 g of $Cr(NO_3)_3.9H_2O$, 3.35 g of $Fe(NO_3)_3.9H_2O$ and 2.13 g of $Mg(NO_3)_2.6H_2O$ were each dissolved separately in $H_2O$, while 4.02 g of $Bi(NO_3)_3.9H_2O$ was dissolved in a 10% $HNO_3$ solution. All of the nitrates solutions were then combined and added to the Mo-W slurry. The resulting light blue slurry was evaporated on a hot plate with constant stirring until it started to thicken. It was then dried at 120° C, denitrified at 290° C. for 3 hours and at 425° C. for 3 hours, ground to a 20-35 mesh size, and calcined at 610° C. for 3 hours.

CATALYST EXAMPLE 5

A catalyst having the composition

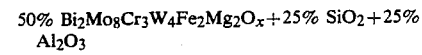

was prepared as follows:

The Procedure was exactly as described in Catalyst Example 4, except that 0.80 g of a 10% $CsNO_3$ solution was added to the nitrates solutions before they were added to the Mo-W solution.

CATALYST EXAMPLE 6

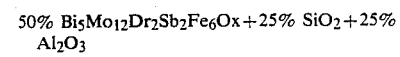

was prepared as follows:

6.88 g of $(NH_4)_6Mo_7O_{24}\cdot 4H_2O$ was dissolved in 200 cc of warm $H_2O$ and 8.76 g of $Sb_2O_5$ sol (12% $Sb_2O_5$) was then added to it. 2.60 g of $Cr(NO_3)_3\cdot 9H_2O$ and 7.88 g of $Fe(NO_3)_3\cdot 9H_2O$ were dissolved separately in $H_2O$, while 7.88 g of $Bi(NO_3)_3\cdot 5H_2O$ was dissolved in a 10% $HNO_3$ solution. The nitrates solutions were then mixed and added to the Ho-Sb mixture. 15.62 g of silica sol (40% $SiO_2$, $NH_4+$ stabilized) and 31.25 g of alumina sol (20% $Al_2O_3$) were then added, and the catalyst slurry was processed exactly as described in Catalyst Example 4.

CATALYST EXAMPLE 7

TABLE 1

| Run Example No. | Catalyst Example No. | Mole Ratios $C_3/NH_3/O_2/H_2O/N_2$ | Temp. °C. | CT Secs | Percent Propane Conversion | Propane: Mole % Conversion to | | | | | % Selectivity Based on Propane | | |
|---|---|---|---|---|---|---|---|---|---|---|---|---|---|
| | | | | | | AN | HCN | AN+ HCN | $C_3=$ | AN+ $C_3=$ | AN | AN+ HCN | AN+ $C_3=$ |
| 1C* | 1C* | 5/1/2/1/0 | 470 | 0.5 | 1.7 | 0.5 | 0.1 | 0.6 | 0.4 | 0.9 | 30.8 | 37.9 | 54.4 |
| 2 | 2 | " | " | " | 5.1 | 3.0 | 0.5 | 3.5 | 0.6 | 3.6 | 59.0 | 69.7 | 70.1 |
| 3 | 3 | " | " | 1.1 | 10.0 | 5.8 | 0.6 | 6.4 | 0.2 | 6.0 | 58.3 | 66.3 | 59.9 |
| 4 | 4 | 3/1/2/1/2 | 470 | 1.5 | 15.5 | 7.0 | 0.4 | 7.4 | 1.1 | 8.1 | 45.1 | 48.0 | 52.2 |
| 5 | 5 | " | " | " | 14.8 | 8.0 | 0.8 | 8.8 | 1.1 | 9.1 | 54.2 | 59.4 | 61.5 |
| 6 | 6 | " | " | " | 13.2 | 6.1 | 0.2 | 6.2 | 1.0 | 7.1 | 45.8 | 47.4 | 53.6 |
| 7 | 2 | 5/1/2/1/0 | " | 1.1 | 11.2 | 6.3 | 0.6 | 6.8 | 0.7 | 7.0 | 56.1 | 61.2 | 62.6 |
| 8 | 7 | 5/0.85/2/0/0 | 496 | 1.9 | 12.3 | 7.0 | 0.8 | 7.8 | 0.6 | 7.6 | 57.1 | 63.8 | 61.8 |
| 9 | 8 | Note (1) | 490 | 2.0 | 8.5 | 4.8 | 0.8 | 5.5 | 0.7 | 5.5 | 56.3 | 65.5 | 64.4 |

*C = Comparative
(1) Mole ratio $C_3/NH_3/O_2/N_2$ was 5/1/2/4.7. Pressure was 10 psig.

This was prepared as in Example Z except that the slurry was spray dried using an air inlet temperature of 600° F. and an outlet temperature of 300° F. The microspheroidal particles were heated for 3 hours at Z90° C. and 3 hours at 4Z5° C. It was then screened to 5% −140 to +170 mesh (Tyler screen gauge), 70% −170 to +325 mesh and 25% −325 mesh. It was then calcined at 630° C. for 3 hours. Its composition was

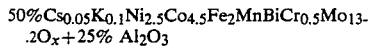
$50\% Cs_{0.05}K_{0.1}Ni_{2.5}Co_{4.5}Fe_2MnBiCr_{0.5}Mo_{13}.2O_x + 25\% Al_2O_3$

CATALYST EXAMPLE 8

In this example "parts" means parts by weight.
The following reagents were used to make a catalyst of the empirical formula

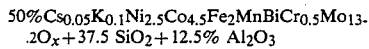
$50\% Cs_{0.05}K_{0.1}Ni_{2.5}Co_{4.5}Fe_2MnBiCr_{0.5}Mo_{13}.2O_x + 37.5\ SiO_2 + 12.5\% Al_2O_3$

| Reagent | Parts |
|---|---|
| $CsNO_3$ - 10% Soln. | 9.75 |
| $KNO_3$ - 10% Soln. | 10.11 |
| $Ni(NO_3)_2\cdot 6H_2O$ | 727.00 |
| $Co(NO_3)_2\cdot 6H_2O$ | 1309.72 |
| $Fe(NO_3)_3\cdot 9H_2O$ | 808.04 |
| $Mn(NO_3)_2$ - 50% Soln. | 357.92 |
| $Bi(NO_3)_3\cdot 5H_2O$ | 485.10 |
| $CrO_3$ | 50.01 |
| $(NH_4)_6Mo_7O_{24}\cdot 4H_2O$ | 2330.65 |
| $SiO_2$ Sol, 40% | 5477.52 |
| $Al_2O_3$ Sol, 20% | 3651.68 |

The ferric nitrate and 150 parts of water were melted on a hot plate with stirring. The other nitrates were then added, one at a time, in the order listed: Mn—, Bi—, Co—, Ni—, K— and Cs—nitrate. The dark brown dispersion was stirred with heating at 60° C.

The ammonium-hepta-molybdate was dissolved in 2300 parts of water at 60° C. The silica sol is then added, followed by the $CrO_3$, which had been diluted with 200 parts of water. An orange dispersion is formed.

The nitrates dispersion was added slowly to the Mo—Si—Cr dispersion forming a yellow slurry. The alumina sol was then added with stirring. The entire mixture was then vigorously blended, and then spray dried and screened and calcined as in Catalyst Example 7, except that the calcination temperature was 550° C.

As will be evident to those skilled in the art, various modifications of this invention can be made or followed in the light of the foregoing disclosure and discussion without departing from the spirit and scope of the disclosure or from the scope of the claims.

We claim:
1. A process for making an $\alpha$, $\epsilon$-unsaturated mononitrile by the catalytic reaction of a paraffin containing 3-5 carbon atoms with molecular oxygen and ammonia by catalytic contact of the foregoing reactants in a reaction zone with a catalyst composition that consists essentially of 10–90 weight percent of a diluent/support and 90–10 weight percent of a metal oxide catalyst containing the elements indicated by the empirical formula,

$A_aD_dBi_cFe_fMo_{12}O_x$ in the proportions indicated by the said formula, said diluent/support containing 10 to 100 weight percent $Al_2O_2$ and zero to 90 weight percent $SiO_2$ wherein
A is one or more of Li, Na, K, Rb, Cs, Tl B, W, Sn and La;
D is one or more of Cr, Sb, Pb, P, Cu, Ni, Co, Mn and Mg;
a is zero to 10;
c is 0.1 to 10;
d is zero to 10; and
f is 0.2 to 10; and
wherein the reactants fed to the reaction zone contain a mole ratio of said paraffin:$NH_3$ in the range from 2 to 16 and a mole ratio of said paraffin to $O_2$ in the range from 1 to 10.

2. A process of claim 1 wherein d is at least 1.
3. A process of claim 1 wherein f is at least 0.6.
4. A process of claim 3 wherein d is at least 1.
5. A process of claim 1 wherein said diluent/support is at least 20 weight percent $Al_2O_3$.
6. A process of claim 1 wherein A is present and includes one or more of Li, Na, K, Cs and W.
7. A process of claim 1 wherein D is present and includes one or more of Cr, Sb, P, Ni, Co, Mn and Mg.
8. A process of claim 6 wherein D is present and includes one or more of Cr, Sb, P, Ni, Co, Mn and Mg.

9. A process of claim 1 wherein A consists essentially of one or more of Li, Na, Cr and W.

10. A process of claim 1 wherein D consists essentially of Cr, Sb, P, Ni, Co, Mn and Mg.

11. A process of claim 2 wherein A includes one or more of Li, Na, K, Cs and W.

12. A process of claim 3 wherein D is present includes one or more of Cr, Sb, P, Ni, Co, Mn and Mg.

13. A process of claim 4 wherein D includes one or more of Cr, Sb, P, Ni, Co, Mn and Mg.

14. A process of claim 5 wherein D includes one or more of Cr, Sb, P, Ni, Co, Mn and Mg.

15. A process according to claim 1 wherein said paraffin is propane.

16. A process according to claim 2 wherein said paraffin is propane.

17. A process according to claim 5 wherein said paraffin is propane.

18. A process of claim 4 wherein said diluent/support is at least 20 weight percent $Al_2O_3$.

19. A process according to claim 18 wherein said paraffin is propane.

* * * * *

UNITED STATES PATENT AND TRADEMARK OFFICE
CERTIFICATE OF CORRECTION

PATENT NO. : 4,978,764

DATED : December 18, 1990

INVENTOR(S) : Michael J. Seely, et al.

It is certified that error appears in the above-identified patent and that said Letters Patent is hereby corrected as shown below:

Column 6, line 45 (claim 1, line 13), please delete the formula "$Al_2O_2$" and substitute therefor --- $Al_2O_3$ ---.

Column 7, line 6 (claim 11, line 1), after "A" insert therefor --- is present and ---.

Column 7, line 9 (claim 12, line 1), after "present" insert therefor --- and ---.

Signed and Sealed this

Twenty-eighth Day of July, 1992

Attest:

DOUGLAS B. COMER

*Attesting Officer*  *Acting Commissioner of Patents and Trademarks*

UNITED STATES PATENT AND TRADEMARK OFFICE
CERTIFICATE OF CORRECTION

PATENT NO. : 4,978,764
DATED : December 18, 1990
INVENTOR(S) : Seely et al It is certified that error appears in the above-identified patent and that said Letters Patent is hereby corrected as shown below:

Column 6; Claim 1, line 1, change "$\alpha,\varepsilon$-unsaturated" to ---$\alpha,\beta$-unsaturated---".

Column 7; Claim 9, line 2, change "Cr" to read ---Cs---.

Signed and Sealed this

Twelfth Day of January, 1993

Attest:

DOUGLAS B. COMER

*Attesting Officer*     Acting Commissioner of Patents and Trademarks